US011928816B2

(12) United States Patent
Wang et al.

(10) Patent No.: US 11,928,816 B2
(45) Date of Patent: Mar. 12, 2024

(54) IMAGE PROCESSING METHOD, APPARATUS, AND SYSTEM, ELECTRONIC DEVICE, AND STORAGE MEDIUM

(71) Applicant: TENCENT TECHNOLOGY (SHENZHEN) COMPANY LIMITED, Shenzhen (CN)

(72) Inventors: Liang Wang, Shenzhen (CN); Jun Zhang, Shenzhen (CN)

(73) Assignee: TENCENT TECHNOLOGY (SHENZHEN) COMPANY LIMITED, Shenzhen (CN)

( * ) Notice: Subject to any disclaimer, the term of this patent is extended or adjusted under 35 U.S.C. 154(b) by 412 days.

(21) Appl. No.: 17/383,359

(22) Filed: Jul. 22, 2021

(65) Prior Publication Data
US 2021/0350537 A1 Nov. 11, 2021

Related U.S. Application Data

(63) Continuation of application No. PCT/CN2020/076518, filed on Feb. 25, 2020.

(30) Foreign Application Priority Data

Feb. 25, 2019 (CN) ......................... 201910138930.6

(51) Int. Cl.
G06T 7/00 (2017.01)
A61B 6/00 (2006.01)
(52) U.S. Cl.
CPC ............ G06T 7/0012 (2013.01); A61B 6/481 (2013.01); A61B 6/502 (2013.01); A61B 6/504 (2013.01);
(Continued)

(58) Field of Classification Search
CPC ........ G16H 50/20; G16H 50/50; G16H 30/40; G16H 20/00; G06T 2207/30101;
(Continued)

(56) References Cited

U.S. PATENT DOCUMENTS 7,106,892 B2 9/2006 Breeuwer et al.
7,599,542 B2 10/2009 Brockway et al.
(Continued)

FOREIGN PATENT DOCUMENTS

CN 1676101 A 10/2005
CN 101069646 A 11/2007
(Continued)

OTHER PUBLICATIONS

Nola, "Dynamic Contrast-Enhanced Magnetic Resonance Imaging as an Imaging Biomarker", 2006 (Year: 2006).*
(Continued)

Primary Examiner — Dung Hong
(74) Attorney, Agent, or Firm — ANOVA LAW GROUP, PLLC

(57) ABSTRACT

An image processing method includes: obtaining DCE magnetic resonance images corresponding to a plurality of time points for a same detection target; determining average pixel grayscale values of images of a same lesion region in the DCE magnetic resonance images of the plurality of time points respectively; determining a time to peak according to the average pixel grayscale values corresponding to the plurality of time points; and generating a first-stage time-intensity image before the time to peak and a second-stage time-intensity image after the time to peak respectively according to the DCE magnetic resonance images and the time to peak. The first-stage time-intensity image and the second-stage time-intensity image are 3D images. A pixel grayscale value of each pixel in the first-stage time-intensity
(Continued)

image and the second-stage time-intensity image represents a change rate of blood supply intensity and reflects a severity level of a lesion corresponding to the lesion region.

20 Claims, 10 Drawing Sheets

(52) U.S. Cl.
CPC .............. G06T 2207/10096 (2013.01); *G06T 2207/30068* (2013.01); *G06T 2207/30096* (2013.01)

(58) Field of Classification Search
CPC . G06T 2207/10088; G06T 2207/30096; G06T 7/0012; G06T 2207/30068; G06T 2207/10096; A61B 6/481; A61B 6/502; A61B 6/504
See application file for complete search history.

(56) References Cited

U.S. PATENT DOCUMENTS

| | | | |
|---|---|---|---|
| 10,176,573 B2 * | 1/2019 | Hou | G06T 7/33 |
| 11,672,499 B2 * | 6/2023 | Tanaka | A61B 6/507 600/407 |
| 11,715,205 B2 * | 8/2023 | Gurevich | G16H 50/50 382/128 |
| 2006/0004279 A1 | 1/2006 | Ikeda et al. | |
| 2007/0265529 A1 | 11/2007 | Hashimoto | |
| 2010/0066756 A1 | 3/2010 | Yang | |
| 2010/0172562 A1 * | 7/2010 | Satoh | G06T 7/0016 382/224 |
| 2011/0188722 A1 * | 8/2011 | Huang | G01R 33/56 382/131 |
| 2012/0027282 A1 * | 2/2012 | Yoshikawa | A61B 8/13 382/131 |
| 2012/0257164 A1 | 10/2012 | Zee et al. | |
| 2015/0196281 A1 | 7/2015 | Takagi et al. | |
| 2016/0350913 A1 * | 12/2016 | Nagae | G06T 7/174 |
| 2018/0109698 A1 | 4/2018 | Ramsay et al. | |
| 2018/0275128 A1 | 9/2018 | Parker | |

FOREIGN PATENT DOCUMENTS

| | | |
|---|---|---|
| CN | 101626726 A | 1/2010 |
| CN | 102247144 A | 11/2011 |
| CN | 102387747 A | 3/2012 |
| CN | 103458772 A | 12/2013 |
| CN | 103514607 A | 1/2014 |
| CN | 103886576 A | 6/2014 |
| CN | 105249990 A | 1/2016 |
| CN | 105879064 A | 8/2016 |
| CN | 107569248 A | 1/2018 |
| CN | 107849614 A | 3/2018 |
| CN | 107949325 A | 4/2018 |
| CN | 108460748 A | 8/2018 |
| CN | 108882902 A | 11/2018 |
| CN | 109242866 A | 1/2019 |
| CN | 109949274 A | 6/2019 |
| EP | 2299405 A2 | 3/2011 |
| JP | 2010022690 A | 2/2010 |
| TW | 201518967 A | 5/2015 |
| WO | 2010014712 A1 | 2/2010 |
| WO | WO-2010014712 A1 * | 2/2010 ............. G01R 33/56 |

OTHER PUBLICATIONS

Jackson, "Analysis of dynamic contrast enhanced MRI", 2004 (Year: 2004).*
Lee et al., "Multilevel analysis of spatiotemporal association features for differentiation of tumor enhancement patterns in breast DCE-MRI", 2010 (Year: 2010).*
Shannon et al., "Textural Kinetics: A Novel Dynamic Contrast-Enhanced (DCE)-MRI Feature for Breast Lesion Classification", 2011 (Year: 2011).*
The World Intellectual Property Organization (WIPO) International Search Report for PCT/CN2020/076518 dated May 27, 2020 6 Pages (including translation).
The State Intellectual Property Office of the People's Republic of China (SIPO) Office Action 1 for for 201910138930.6 dated Aug. 4, 2020 9 Pages (including translation).
Taiwan Intellectual Property Office Examination report for Application No. 10920656290 dated Jul. 10, 2020 12 pages (including translation).
The State Intellectual Property Office of the People's Republic of China (SIPO) Office Action 1 for 201910755538.6 dated Aug. 26, 2020 14 Pages (including translation).
Hui Liu et al., "Total variation based DCE-MRI decomposition by separating lesion from background for time-intensity curve estimation," Medical Physics, vol. 44, Issue 6, Mar. 30, 2017 (Mar. 30, 2017). 26 pages.
Xiaodong Xu, "Hemodynamics of breast disease changes MRI image analysis," Modern Chinese Medicine Application, vol. 8, Issue 3, Feb. 10, 2014 (Feb. 10, 2014). 3 pages.
Ke Li et al., "Feature selection and analysis of DCE-MRI in breast computer-aided diagnosis," Beijing Biomedical Engineering, vol. 31, No. 4, Aug. 31, 2012 (Aug. 31, 2012), pp. 344-345. 6 pages.
Mengling Wu, "Relating doses of contrast angent administered to time-intensity curve and semi-quantitative parameters on DCE-MRI," Chinese Master's Theses Full-text Database, Medicine and Health Sciences, Jan. 15, 2015 (Jan. 15, 2015), p. 7. 5 pages.
Shuang Gu et al., "Clinical significance of time-signal intensity curve type I on dynamic contrast-enhanced MRI of the breasts," Chinese Journal of Magnetic Resonance Imaging, 2011, vol. 2, No. 3, pp. 190-194. 5 pages.
The European Patent Office (EPO) The Extended European Search Report for 20762231.7 dated Mar. 17, 2022 9 Pages.
Ahmed B Ashraf et al., "A Multichannel Markov Random Field Approach for Automated Segmentation of Breast Cancer Tumor in DCE-MRI Data Using Kinetic Observation Model," Medical Image Computing and Computer-Assisted Intervention (MICCAI 2011), Part III, LNCS 6893, Springer Berlin, Heidelberg, pp. 546-553, 2011. 8 pages.

* cited by examiner

IMAGE PROCESSING METHOD, APPARATUS, AND SYSTEM, ELECTRONIC DEVICE, AND STORAGE MEDIUM

CROSS-REFERENCES TO RELATED APPLICATIONS

This application is a continuation application of PCT Patent Application No. PCT/CN2020/076518, entitled "IMAGE PROCESSING METHOD, APPARATUS AND SYSTEM, AND ELECTRONIC DEVICE AND STORAGE MEDIUM" and filed on Feb. 25, 2020, which claims priority to Chinese Patent Application No. 201910138930.6, filed with China National Intellectual Property Administration on Feb. 25, 2019 and entitled "IMAGE PROCESSING METHOD, APPARATUS AND SYSTEM", the entire contents of both of which are incorporated herein by reference.

FIELD OF THE TECHNOLOGY

The present disclosure relates to the field of medical image processing technologies, and in particular, to an image processing method, apparatus, and system, an electronic device, and a storage medium.

BACKGROUND OF THE DISCLOSURE

Currently, in the analysis of images of magnetic resonance imaging (MRI) of breast tumors, the analysis is generally performed by generating a corresponding time-intensity curve (TIC) based on dynamic contrast enhanced (DCE) images, which has a certain value. Usually, the TIC is mainly generated in the following manner: DCE magnetic resonance images of a plurality of time points are obtained by using conventional breast MRI, then a point is selected from a suspect lesion region, to obtain pixel grayscale values corresponding to the point in the DCE magnetic resonance images of different time points, and a curve is drawn, that is, the TIC. In this way, a breast tumor diagnosis result may be determined based on the TIC.

SUMMARY

Embodiments of the present disclosure provide an image processing method, apparatus, and system, an electronic device, and a storage medium, to resolve a problem that in the related art, only a one-dimensional curve can be generated, which provides relatively one-sided reference, and thus a lesion region cannot be expressed completely and accurately.

Specific technical solutions provided in the embodiments of the present disclosure are as follows.

An embodiment of the present disclosure provides an image processing method, performed by an electronic device, the method including: obtaining DCE magnetic resonance images corresponding to a plurality of time points for a same detection target; determining average pixel grayscale values of images of a same lesion region in the DCE magnetic resonance images of the plurality of time points respectively; determining a time to peak according to the average pixel grayscale values corresponding to the plurality of time points; and generating a first-stage time-intensity image before the time to peak and a second-stage time-intensity image after the time to peak respectively according to the DCE magnetic resonance images of the plurality of time points and the time to peak. The first-stage time-intensity image and the second-stage time-intensity image are 3D images. A pixel grayscale value of each pixel in the first-stage time-intensity image and the second-stage time-intensity image represents a change rate of blood supply intensity and reflects a severity level of a lesion corresponding to the lesion region.

Another embodiment of the present disclosure provides an image processing apparatus, including: an obtaining module, configured to obtain dynamic contrast enhanced (DCE) magnetic resonance images corresponding to a plurality of time points for the same detection target; a first determining module, configured to determine average pixel grayscale values of images of the same lesion region in the DCE magnetic resonance images of the plurality of time points respectively; a second determining module, configured to determine a time to peak according to the average pixel grayscale values corresponding to the plurality of time points; and a generation module, configured to generate a first-stage time-intensity image before the time to peak and a second-stage time-intensity image after the time to peak respectively according to the DCE magnetic resonance images of the plurality of time points and the time to peak, the first-stage time-intensity image and the second-stage time-intensity image being 3D images, a pixel grayscale value of each pixel in the first-stage time-intensity image and the second-stage time-intensity image representing a change rate of blood supply intensity and reflecting a severity level of the lesion.

Another embodiment of the present disclosure provides an image processing system, including: an image acquisition device, configured to obtain dynamic contrast enhanced (DCE) magnetic resonance images corresponding to a plurality of time points for the same detection target; an image processing device, configured to respectively determine average pixel grayscale values of images of the same lesion region in the DCE magnetic resonance images of the plurality of time points, determine a time to peak according to the average pixel grayscale values corresponding to the plurality of time points, and generate a first-stage time-intensity image before the time to peak and a second-stage time-intensity image after the time to peak respectively according to the DCE magnetic resonance images of the plurality of time points and the time to peak, the first-stage time-intensity image and the second-stage time-intensity image being 3D images, a pixel grayscale value of each point in the first-stage time-intensity image and the second-stage time-intensity image representing a change rate of blood supply intensity and reflecting a severity level of the lesion; and a display device, configured to output and display the first-stage time-intensity image and the second-stage time-intensity image.

Another embodiment of the present disclosure provides an electronic device, including: at least one memory, configured to store program instructions; and at least one processor, configured to invoke the program instructions stored in the memory, to perform a plurality of operations. The operations include: obtaining DCE magnetic resonance images corresponding to a plurality of time points for a same detection target; determining average pixel grayscale values of images of a same lesion region in the DCE magnetic resonance images of the plurality of time points respectively; determining a time to peak according to the average pixel grayscale values corresponding to the plurality of time points; and generating a first-stage time-intensity image before the time to peak and a second-stage time-intensity image after the time to peak respectively according to the DCE magnetic resonance images of the plurality of time points and the time to peak. The first-stage time-intensity image and the second-stage time-intensity image are 3D images. A pixel grayscale value of each pixel in the first-stage time-intensity image and the second-stage time-intensity image represents a change rate of blood supply intensity and reflects a severity level of a lesion corresponding to the lesion region.

Another embodiment of the present disclosure provides a non-transitory computer-readable storage medium, storing a computer program, the computer program, when executed by a processor, cause the processor to perform: obtaining DCE magnetic resonance images corresponding to a plurality of time points for a same detection target; determining average pixel grayscale values of images of a same lesion region in the DCE magnetic resonance images of the plurality of time points respectively; determining a time to peak according to the average pixel grayscale values corresponding to the plurality of time points; and generating a first-stage time-intensity image before the time to peak and a second-stage time-intensity image after the time to peak respectively according to the DCE magnetic resonance images of the plurality of time points and the time to peak. The first-stage time-intensity image and the second-stage time-intensity image are 3D images. A pixel grayscale value of each pixel in the first-stage time-intensity image and the second-stage time-intensity image represents a change rate of blood supply intensity and reflects a severity level of a lesion corresponding to the lesion region.

DESCRIPTION OF EMBODIMENTS

Figure 1:
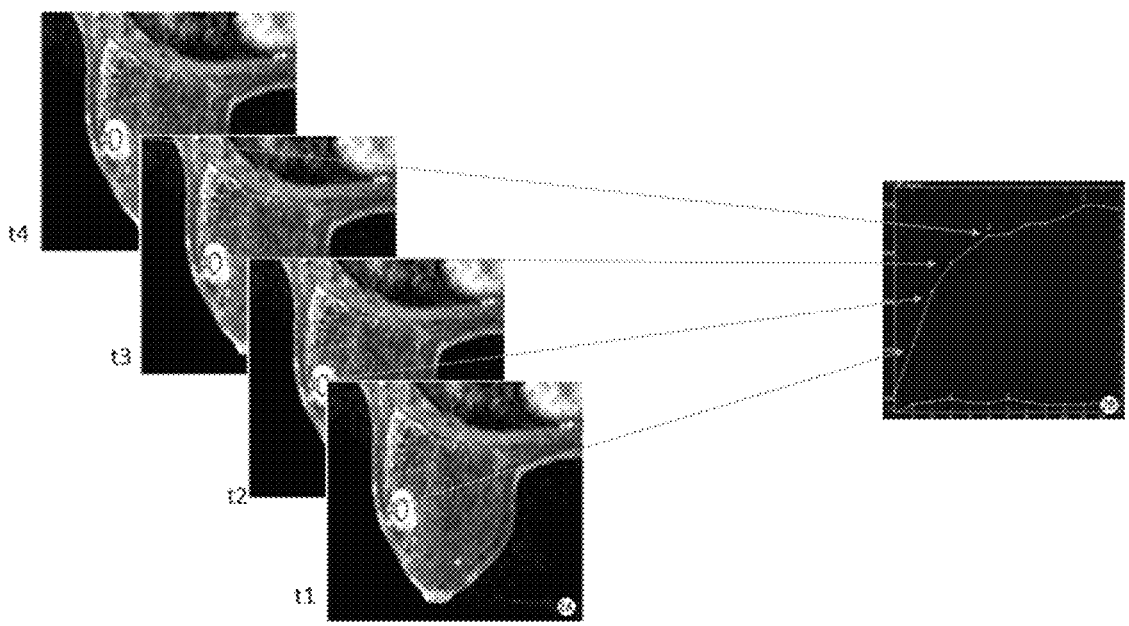
FIG. 1 is a schematic diagram of a conventional TIC generating principle.

The following clearly and completely describes the technical solutions in embodiments of the present disclosure with reference to the accompanying drawings in the embodiments of the present disclosure. Apparently, the described embodiments are some of the embodiments of the present disclosure rather than all of the embodiments. All other embodiments obtained by a person of ordinary skill in the art based on the embodiments of the present disclosure without creative efforts shall fall within the protection scope of the present disclosure.

To facilitate the understanding of the embodiments of the present disclosure, the following concepts are briefly introduced.

Contrast agent: also referred to as a contrast medium, which is a chemical product injected or taken into a human tissue or organ for enhancing image observation effects, where densities of the products are greater than or less than those of surrounding tissues, and formed contrast is displayed in images by using some instruments.

Magnetic resonance imaging (MRI): one type of tomography, which mainly obtains electromagnetic signals from human bodies by using a magnetic resonance phenomenon, and reconstructs human body information.

Dynamic contrast enhancement: physical and physiological properties of an organ or a tissue may be reflected by a level of signal enhancement. In practice, multi-temporal scanning may be performed based on DCE-MRI, to generate continuous dynamic images, and a series of semi-quantitative and quantitative parameters can be obtained by using a post-processing technology, to reflect enhancement features of a lesion more objectively, thereby providing richer and more complete information of physiological properties of a displayed region.

Time-intensity curve (TIC): a curve based on MRI dynamic enhanced scanning, that is, a time-intensity curve generated by DCE-MRI. A TIC may reflect changes of image brightness of a tissue over time when the tissue is infused with a contrast medium. A qualitative analysis, grading, and other analyses may be performed for a lesion, such as a tumor, by observing a flow-in speed and an amount of the contrast medium in a lesion region, which has a certain value. A horizontal coordinate of the TIC represents time, and a vertical coordinate of the TIC represents a pixel grayscale value of a point in an image.

In addition, for a better understanding, meanings represented by the TIC are now described. TICs may be classified as follows: type I, which is a continuously rising type, that is, after a contrast medium is injected, signal intensity of a lesion keeps rising, and the lesion showing the type I curve tends to be a benign lesion; type II, which is a platform type, that is, in a certain period of time after injection of a contrast medium, signal intensity of a lesion rises to a certain level, and then the signal intensity does not change obviously in a relatively long period of time; and type III, which is a flow-out type, that is, after a contrast medium is injected, signal intensity of a lesion rises to a certain level, and then decreases gradually, which is a fast-in fast-out type. Most of the type III TICs represent malignant lesions.

Time to peak: a time at which a peak value is reached, which is mainly a time point with a largest change of signal intensity on a TIC in the embodiments of the present disclosure.

Region of interest (ROI): a local region on original data. In the embodiments of the present disclosure, the ROI represents a 2-dimension (2D) or a 3-dimension (3D) rectangular region, and refers to a certain lesion region.

Lesion: a part with a lesion on an organism.

Grayscale value: representing a brightness value of a single pixel of a grayscale image. A larger value indicates that the pixel is brighter, and a smaller value indicates that the pixel is darker. The grayscale value may be used for describing a brightness value of a specific pixel in the image.

In an analysis of images of MRI of breast tumors, the analysis is generally performed by generating a corresponding TIC based on DEC images. Specifically, FIG. 1 is a schematic diagram of a conventional TIC generating principle. Through magnetic resonance scanning, DCE magnetic resonance images of a plurality of time points are obtained; a point is selected from a suspect lesion region, to obtain pixel grayscale values corresponding to the point in the DCE magnetic resonance images of different time points, and a curve is drawn, that is, the TIC. For example, as shown in FIG. 1, DCE magnetic resonance images of 4 time points of a point are listed, which are DCE magnetic resonance images of t1, t2, t3, and t4, respectively, and a TIC of the point is obtained, shown in the right part of FIG. 1. A horizontal coordinate of the TIC represents a time point, and a vertical coordinate of the TIC represents a pixel grayscale value of the point.

However, the TIC generated in the foregoing method is a one-dimensional curve, which can only express changes of pixel values of a small region, and when the TIC is drawn, points are selected manually, which is random. Different doctors may select different points, but different points may bring about different diagnosis results, which is relatively one-sided, and thus a lesion region cannot be expressed completely and accurately.

Therefore, for the foregoing problem, an embodiment of the present disclosure provides an image generation method. 3D images may be generated based on DCE magnetic resonance images, a conventional TIC is replaced with two 3D images, and information expressed by the TIC is expressed by the two 3D images. After DCE magnetic resonance images corresponding to a plurality of time points for the same detection target are obtained, average pixel grayscale values of images of the same lesion region in the DCE magnetic resonance images of the plurality of time points are determined, a time to peak is calculated, and then a first-stage time-intensity image before the time to peak and a second-stage time-intensity image after the time to peak are generated respectively according to the time to peak and the DCE magnetic resonance images of the plurality of time points. A pixel grayscale value of each point (i.e., each pixel) of the first-stage time-intensity image and the second-stage time-intensity image represents a change rate of blood supply intensity of the lesion region, which may reflect a severity level of the lesion region, so that the severity level of the lesion may be determined according to the pixel grayscale values of the first-stage time-intensity image and the second-stage time-intensity image, that is, brightness changes. Therefore, a 3D first-stage time-intensity image and a 3D second-stage time-intensity image may be generated, a larger amount of more complete lesion information can be provided, to show an overall situation of a lesion of a detection target, which is more complete and intuitive. In addition, specific quantitative information may further be provided, to provide more accurate and reliable diagnosis bases, thereby improving the accuracy of lesion diagnosis.

Figure 2A:
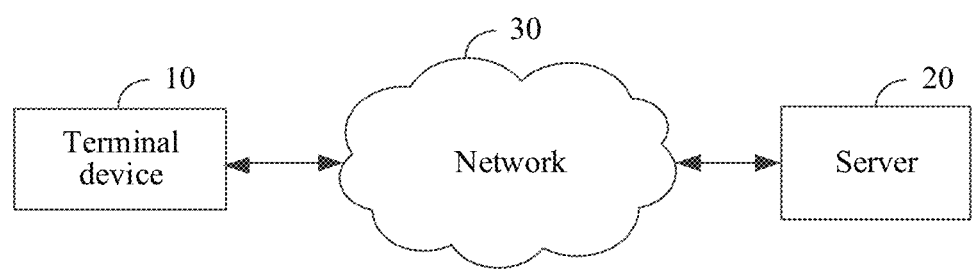
FIG. 2A is a schematic diagram of an implementation environment of an image processing method according to an embodiment of the present disclosure.

FIG. 2A is a schematic diagram of an implementation environment of an image processing method according to an embodiment of the present disclosure. As shown in FIG. 2A, the image processing method in the embodiments of the present disclosure may be performed by a terminal device 10, for example, a corresponding medical device, or may be performed by a server 20. For example, the terminal device 10 transmits obtained DCE magnetic resonance images of a plurality of time points to the server 20. The server 20 determines a time to peak, and generates a first-stage time-intensity image before the time to peak and a second-stage time-intensity image after the time to peak. The generated first-stage time-intensity image and second-stage time-intensity image may be transmitted to the terminal device 10. The terminal device 10 may display the generated first-stage time-intensity image and second-stage time-intensity image. The terminal device 10 may be connected to the server 20 through a network 30, to implement intercommunication. The network 30 may be a wired network, or may be a wireless network. The server 20 may be considered as a backend server providing a corresponding network service. The embodiments of the present disclosure do not impose any limitation on the two manners.

In addition, in the embodiments of the present disclosure, the analysis of MRI images of breast tumors is mainly used as an example for description; certainly, the analysis is also applicable to other application scenarios. This is not limited in the embodiments of the present disclosure.

Figure 2B:
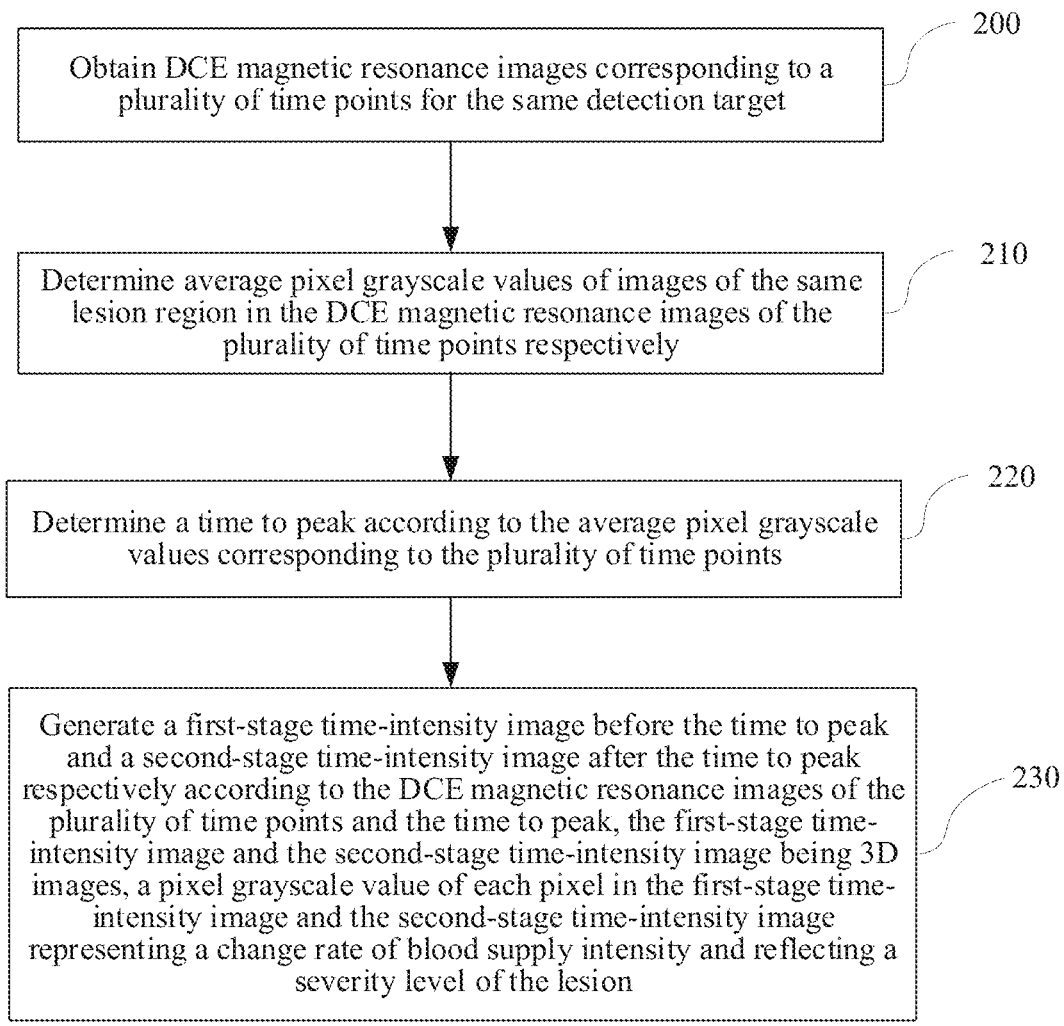
FIG. 2B is a flowchart of an image processing method according to an embodiment of the present disclosure.

FIG. 2B is a flowchart of an image processing method according to an embodiment of the present disclosure. The method includes the following steps:

Step 200: Obtain DCE magnetic resonance images corresponding to a plurality of time points for the same detection target.

The detection target, for example, is an organ or a tissue of a human body.

For example, during analysis of a breast tumor, based on a magnetic resonance scanning instrument such as an MRI scanner, after scanning parameters are set, for example, parameters such as a scanning time and a scanning interval may be set, a breast may be scanned, to obtain DCE magnetic resonance images corresponding to a plurality of time points for the breast.

Further, because a main objective in the embodiments of the present disclosure is to analyze a lesion, such as a tumor, a lesion region further needs to be determined in the DCE magnetic resonance images. An embodiment of the present disclosure provides an implementation: a lesion region is determined in the DCE magnetic resonance images according to a preset image segmentation algorithm and lesion features.

In the embodiments of the present disclosure, 3D DCE magnetic resonance images may be obtained after MRI scanning, and a suspect lesion region, such as a tumor region, may be automatically determined on the 3D DCE magnetic resonance images according to the image segmentation algorithm. The suspect lesion region may be determined in one DCE magnetic resonance image, or may be determined in each of the DCE magnetic resonance images respectively. Of course, the lesion region may alternatively be determined in another manner. This is not limited in the embodiments of the present disclosure.

Figure 3:
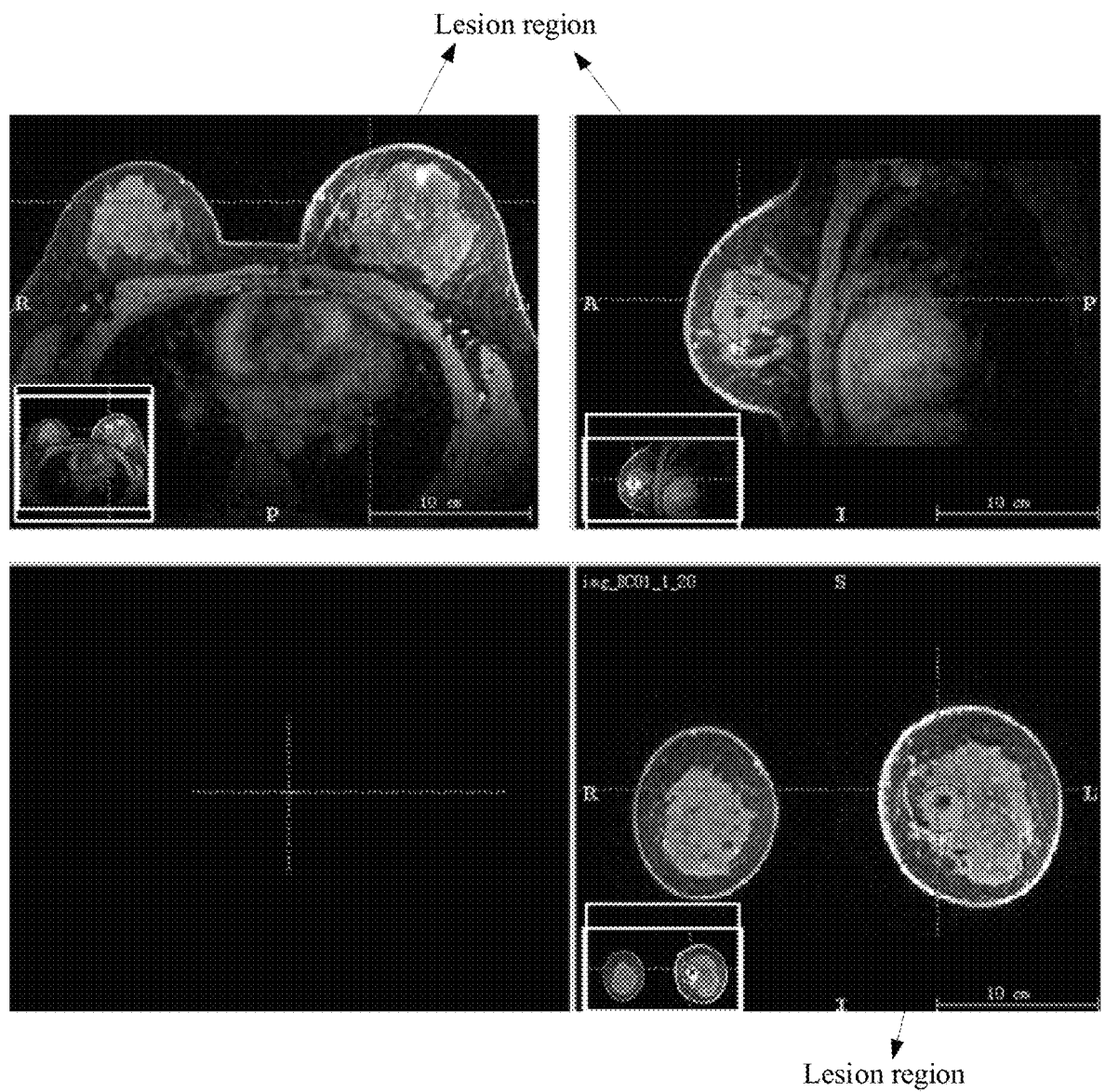
FIG. 3 is a three-view diagram of DCE magnetic resonance images of 3D breast MRI according to an embodiment of the present disclosure.

Using breast MRI as an example, FIG. 3 is a three-view diagram of DCE magnetic resonance images of 3D breast MRI according to an embodiment of the present disclosure. In FIG. 3, an upper left image is a cross-sectional view, an upper right image is a sagittal plane view, and a lower right image is a coronal plane view (there is no image at the lower left part, which may be not considered). Through image segmentation, the lesion region may be determined. 3D regions shown in circles in the upper left image, the upper right image, and the lower right image in FIG. 3 are determined lesion regions. Highlighted circle regions at the intersection of two dotted lines shown in the upper left image, the upper right image, and the lower right image in FIG. 3 are actual tumor positions. Therefore, it may be learned that, the determined lesion region is basically accurate.

Step 210: Determine average pixel grayscale values of images of the same lesion region in the DCE magnetic resonance images of the plurality of time points respectively.

In practice, each time point corresponds to one DCE sequence, that is, one DCE magnetic resonance image. In the embodiments of the present disclosure, for a DCE magnetic resonance image of any time point, all pixel grayscale values in the lesion region are determined, an average pixel grayscale value is calculated, and the average pixel grayscale value is used as a grayscale value of the current time point. Therefore, there is no need to select a point from the lesion region for calculation; instead, the average pixel grayscale value is calculated, which can improve accuracy and express features of the entire lesion region more accurately.

Step 220: Determine a time to peak according to the average pixel grayscale values corresponding to the plurality of time points.

Step 220 specifically includes the following steps:

Step S1: Generate a TIC of the same lesion region according to the average pixel grayscale values corresponding to the plurality of time points.

That is, based on the plurality of time points, and the average pixel grayscale values corresponding to the plurality of time points, a TIC is generated, where a horizontal axis of the TIC represents an index value of time, and a vertical axis of the TIC represents an average pixel grayscale value of the lesion region.

Step S2: Determine a first-order gradient curve corresponding to the TIC, and use a time point corresponding to a highest point on the corresponding first-order gradient curve as the time to peak.

In an embodiment of the present disclosure, a time to peak is a point on the TIC with a largest change of signal intensity. During calculation of the point with the largest change of signal intensity, a first-order gradient curve corresponding to the TIC may be calculated first. Because a gradient may reflect an amount of change, a highest point on the first-order gradient curve is the point with the largest change of signal intensity, and the point is used as the time to peak.

Figure 4A:
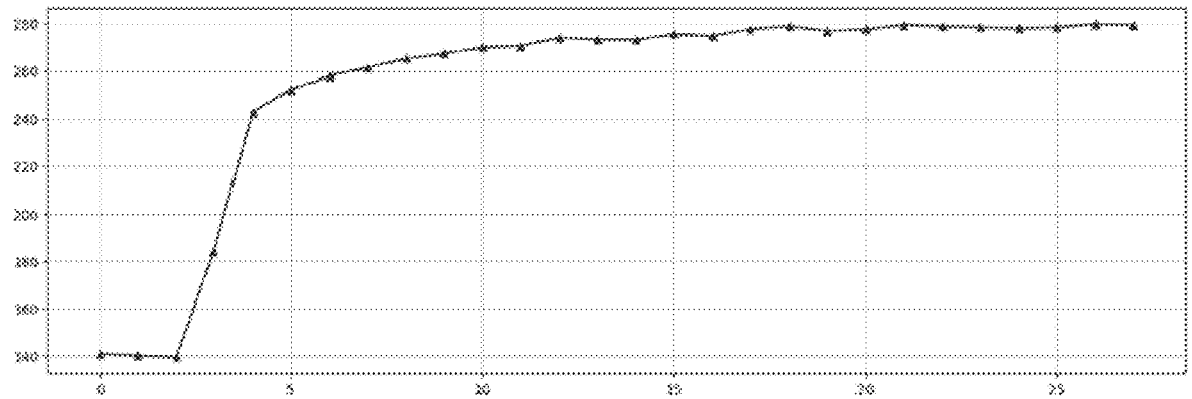
FIG. 4A is a schematic diagram of a TIC of a 3D lesion region according to an embodiment of the present disclosure.
Figure 4B:
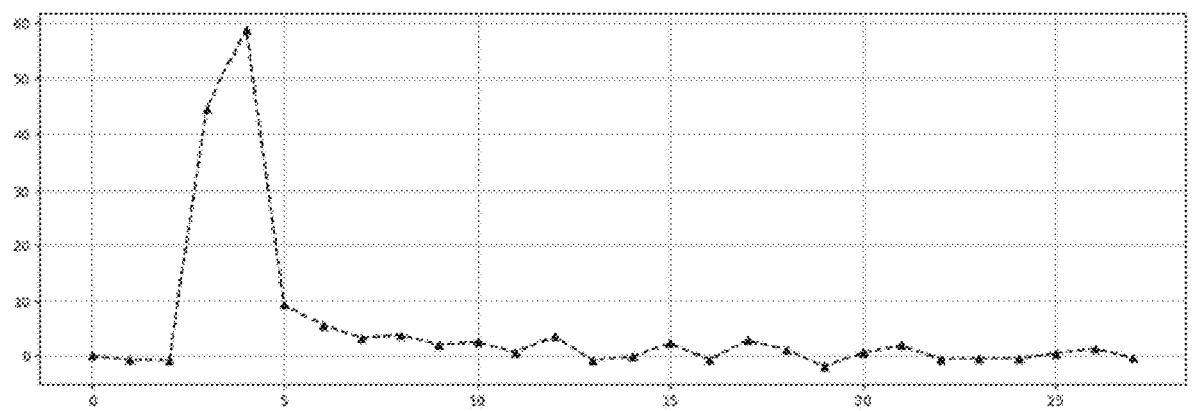
FIG. 4B is a schematic diagram of a first-order gradient curve corresponding to a TIC according to an embodiment of the present disclosure.

For example, FIG. 4A is a schematic diagram of a TIC of a 3D lesion region according to an embodiment of the present disclosure. FIG. 4B is a schematic diagram of a first-order gradient curve corresponding to a TIC according to an embodiment of the present disclosure. By using DCE magnetic resonance images of 28 different time points as an example, as shown in FIG. 4A, horizontal coordinates are time points 0 to 27, and vertical coordinates are average pixel grayscale values corresponding to the time points. A first-order gradient curve corresponding to the TIC of FIG. 4A is calculated, as shown in FIG. 4B. It may be learned that, a time index 4 corresponds to a highest point of the first-order gradient curve, and thus, it may be obtained that the time to peak is 4. In addition, such a TIC may be usually divided into first-stage time-intensity and second-stage time-intensity. By using the time to peak as a segmentation point, that is, when the time index is 4, the first-stage time-intensity of the TIC ends, and the second-stage time-intensity starts.

Step 230: Generate a first-stage time-intensity image before the time to peak and a second-stage time-intensity image after the time to peak respectively according to the DCE magnetic resonance images of the plurality of time points and the time to peak, the first-stage time-intensity image and the second-stage time-intensity image being 3D images, a pixel grayscale value of each point in the first-stage time-intensity image and the second-stage time-intensity image representing a change rate of blood supply intensity and reflecting a severity level of the lesion.

Step 230 may be performed in the following manners:
First manner: generating a first-stage time-intensity image before the time to peak and a second-stage time-intensity image after the time to peak respectively, including the following steps:

Step S1: Determine a start time point and an end time point in the plurality of time points.

For example, as shown in FIG. 4A, a start time point is an index 0, and an end time point is an index 27.

Step S2: Generate the first-stage time-intensity image before the time to peak according to a difference value between the DCE magnetic resonance image of the time to peak and the DCE magnetic resonance image of the start time point.

In an embodiment of the present disclosure, the first-stage time-intensity image represents a time-intensity image calculated for a first stage of the TIC. For example, as shown in FIG. 4A, a start time point of the first-stage time-intensity image is a time index 0, and an end time point is the time to peak, which is an index 4. A first-stage time-intensity image may be calculated according to a difference value between DCE magnetic resonance images corresponding to the time index 0 and the time index 4.

For example, the first-stage time-intensity image is denoted by TI1, a DCE magnetic resonance image with a value of a time index being t is denoted by $I_{DCE}(t)$, and then the first-stage time-intensity image may be represented as:

$$TI1 = 100\% * \frac{I_{DCE}(4) - I_{DCE}(0)}{I_{DCE}(0) + \delta}.$$

$\delta$ is an infinitely small amount, and to avoid a scenario that a denominator is 0 during calculation, "*" is multiplication.

TI1 may represent an incremental percentage of a first-stage signal at the time to peak relative to $I_{DCE}(0)$, that is, a pixel grayscale value of each point in the first-stage time-intensity image represents a change rate of blood supply intensity, which may reflect a severity level of a lesion.

Step S3: Generate the second-stage time-intensity image after the time to peak according to a difference value between the DCE magnetic resonance image of the end time point and the DCE magnetic resonance image of the time to peak.

In an embodiment of the present disclosure, the second-stage time-intensity image represents a time-intensity image calculated for a second stage of the TIC. For example, as shown in FIG. 4A, a start time point of the second-stage time-intensity image is the time to peak, which is a time index 4, and an end time point is an index 27. A second-stage time-intensity image may be calculated according to a difference value between DCE magnetic resonance images corresponding to the time index 27 and the time index 4.

For example, the second-stage time-intensity image is denoted by TI2, a DCE magnetic resonance image with a value of a time index being t is denoted by $I_{DCE}(t)$, and then the second-stage time-intensity image may be represented as:

$$TI2 = 100\% * \frac{I_{DCE}(27) - I_{DCE}(4)}{I_{DCE}(4) + \delta}.$$

TI2 may represent an incremental percentage of an index of a time point at the end of a second-stage signal, for example, a grayscale change of a DCE magnetic resonance image of t=27, relative to $I_{DCE}(4)$, that is, a pixel grayscale value of each point in the second-stage time-intensity image may also represent a change rate of blood supply intensity, which may reflect a severity level of a lesion.

Second manner: generating a first-stage time-intensity image before the time to peak and a second-stage time-intensity image after the time to peak respectively, including the following steps:

Step S1: Determine a start time point and an end time point in the plurality of time points, and sample a preset quantity of time points from the plurality of time points.

For example, sampling may be performed according to actual requirements, and a plurality of time points may be selected from the time points.

Step S2: Determine first difference values between the DCE magnetic resonance images of the time points sampled before the time to peak and the DCE magnetic resonance image of the start time point respectively, and generate the first-stage time-intensity image before the time to peak according to an average value of the first difference values.

For example, the sampled time points are 3, 4, 8, and 25, and the time to peak is 4; in this case, the calculated first-stage time-intensity image may be represented as:

$$TI1 = \left(100\% * \frac{I_{DCE}(4) - I_{DCE}(0)}{I_{DCE}(0) + \delta} + 100\% * \frac{I_{DCE}(3) - i_{DCE}(0)}{I_{DCE}(0) + \delta}\right)/2.$$

Step S3: Determine second difference values between the DCE magnetic resonance images of the time points sampled after the time to peak and the DCE magnetic resonance image of the time to peak respectively, and generate the second-stage time-intensity image after the time to peak according to an average value of the second difference values.

For example, the calculated second-stage time-intensity image may be represented as:

$$TI2 = \left(100\% * \frac{I_{DCE}(8) - I_{DCE}(4)}{I_{DCE}(4) + \delta} + 100\% * \frac{I_{DCE}(25) - I_{DCE}(4)}{I_{DCE}(4) + \delta}\right)/2.$$

In the embodiments of the present disclosure, generation of the first-stage time-intensity image and the second-stage time-intensity image is not limited to the foregoing two manners. For example, the first-stage time-intensity image may further be represented by using a difference value between a point, which is different from the time to peak, before the time to peak and the start time point; the second-stage time-intensity image may further be represented by using a difference value between a point after the time to peak and the time to peak. The generation manner may be specifically set according to actual requirements and situations, and is not limited in the embodiments of the present disclosure. The objective is to generate 3D images that may represent the change of image grayscale values before and after the time to peak.

Therefore, in the embodiments of the present disclosure, because DCE magnetic resonance images are 3D images, the first-stage time-intensity image and the second-stage time-intensity image generated based on change rates of image grayscale values are also 3D images. In addition, when MRI scanning is performed, after a contrast medium (that is, a contrast agent) is injected, if there is a lesion such as a tumor, as time changes, image brightness (that is, image signal intensity) changes differently than in a normal situation. Therefore, a pixel grayscale value of each point in the first-stage time-intensity image and the second-stage time-intensity image generated by using changes of image grayscale values may be used for determining a lesion region and a severity level of the lesion region. A greater grayscale value means the image is brighter, and indicates a higher lesion possibility. A lesion level may be determined according to pixel grayscale values of the lesion regions in the first-stage time-intensity image and the second-stage time-intensity image. For example, it may be determined whether a tumor is a benign tumor or a malignant tumor. For example, pixel grayscale values of the lesion region in the first-stage time-intensity image are positive values and are greater than a specific threshold, and pixel grayscale values of the lesion region in the second-stage time-intensity image are negative values and are less than a specific threshold, which means that an increment of the grayscale values increases gradually, and then decreases. This is similar to a fast-in fast-out type TIC, representing that a severity level of the lesion region is higher than a preset level. That is, generally, the tumor may be determined as a malignant tumor.

Figure 5A:
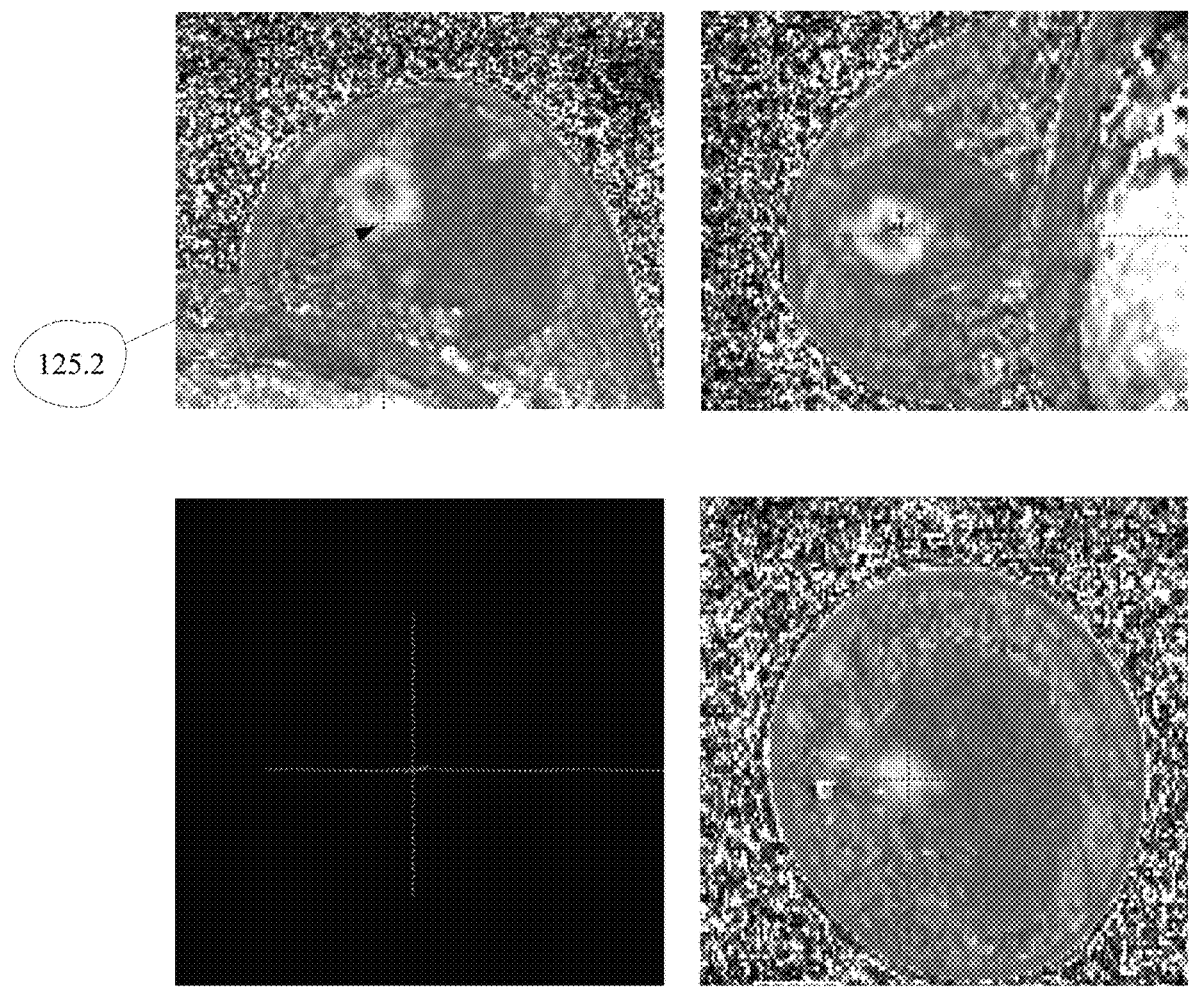
FIG. 5A is a schematic diagram of a first-stage time-intensity image according to an embodiment of the present disclosure.

For example, FIG. 5A is a schematic diagram of a first-stage time-intensity image according to an embodiment of the present disclosure. As shown in the upper left image in FIG. 5A, an intersection of two dotted lines represents a point in a lesion region. It may be seen that a grayscale value of the point is 125.2, which means that brightness of $I_{DCE}(4)$ increases by 125.2% relative to $I_{DCE}(0)$, and a pixel grayscale value increases.

Figure 5B:
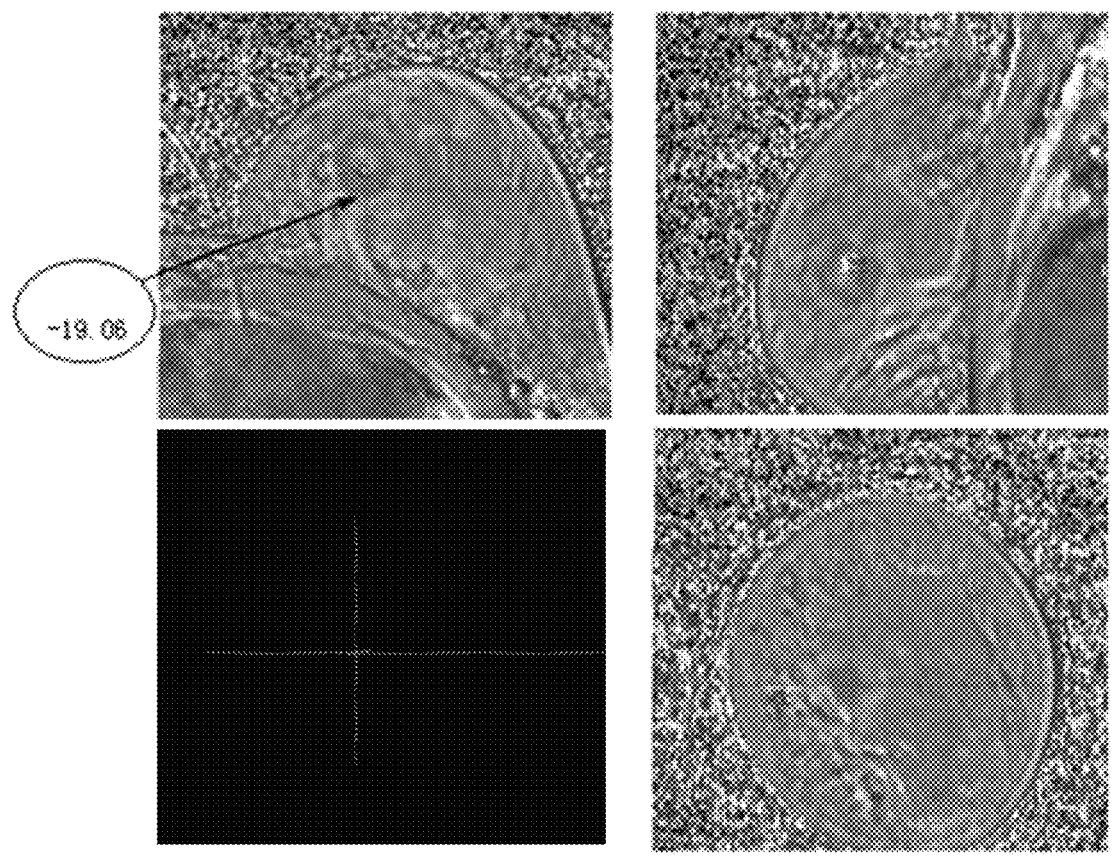
FIG. 5B is a schematic diagram of a second-stage time-intensity image according to an embodiment of the present disclosure.

FIG. 5B is a schematic diagram of a second-stage time-intensity image according to an embodiment of the present disclosure. As shown in the upper left image in FIG. 5B, an intersection of two dotted lines represents a point in a lesion region. It may be seen that a grayscale value of the point is −19.06, which means that brightness of $I_{DCE}(27)$ decreases by 19.06% relative to $I_{DCE}(4)$, and a pixel grayscale value decreases. By analyzing a plurality of points in the lesion region, it may be learned that pixel grayscale values increase gradually and then decrease, and it is highly possible that the lesion region is a tumor.

Figure 6A:
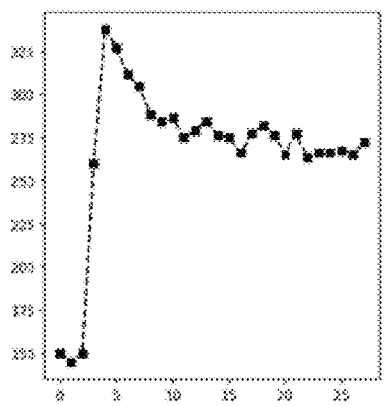
FIGS. 6A-6C are schematic diagrams of a TIC of a point in another lesion region according to an embodiment of the present disclosure.
Figure 6B:
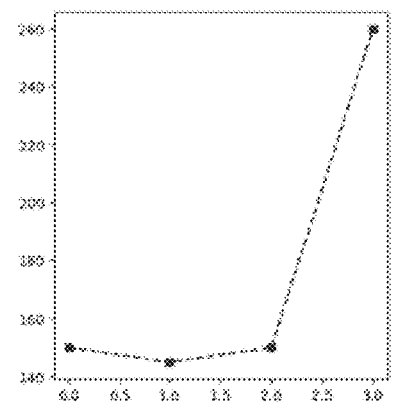
Figure 6C:
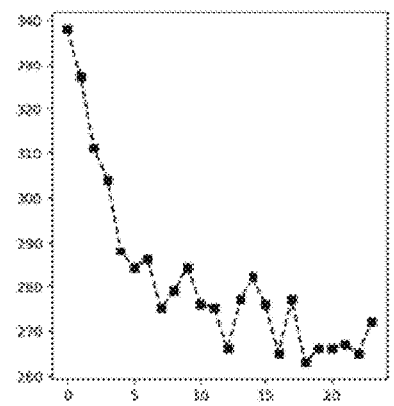

In addition, by mapping to a TIC, a similar conclusion may be obtained. For example, FIGS. 6A-6C are schematic diagrams of a TIC of a point in another lesion region according to an embodiment of the present disclosure. FIG. 6A shows the entire TIC, FIG. 6B is a schematic diagram of a TIC before a time to peak, and FIG. 6C is a schematic diagram of a TIC after a time to peak. A point in FIGS. 6A-6C refers to a pixel at the intersection of two dotted lines in FIG. 5A and FIG. 5B. It may be learned that a TIC corresponding to the point is of a fast-in fast-out type, and it is more likely that the tumor is a malignant tumor.

Further, colors corresponding to different pixel grayscale values may be set. In some embodiments, an intensity of a first color (e.g., intensity of red color) indicates an increasing extent in brightness of a pixel grayscale value, and an intensity of a second color (e.g., intensity of blue color) indicates a decreasing extent in brightness of a pixel grayscale value. A third color (e.g., a white color) indicates no change in brightness of a pixel grayscale value. That is, when the pixel grayscale value changes are a greater negative value, a smaller negative value, 0, a smaller positive value, or a greater positive value, the corresponding colors are respectively a darker blue, a lighter blue, white, a lighter red, and a darker red. For example, positive grayscale value changes (i.e., positive change rate of blood supply) gradually increase from white to red, negative grayscale value changes (i.e., negative change rate of blood supply) gradually decrease from white to blue. In this case, the white color in the first-stage time-intensity image and the second-stage time-intensity image may represent that a small brightness difference, the red color may represent that the brightness increases, and the blue color represents that the brightness decreases, so that a lesion level may be directly determined according to color changes in the first-stage time-intensity image and the second-stage time-intensity image, which is more intuitive.

In the embodiments of the present disclosure, based on the obtained DCE magnetic resonance images, average pixel grayscale values of images of the same lesion region in the DCE magnetic resonance images of the plurality of time points are respectively determined, and according to the average pixel grayscale values corresponding to the plurality of time points, a time to peak is determined; according to the DCE magnetic resonance images of the plurality of time points and the time to peak, a first-stage time-intensity image before the time to peak and a second-stage time-intensity image after the time to peak are generated respectively. Therefore, based on the DCE magnetic resonance images, two 3D images are generated, to replace a conventional one-dimensional TIC. The conventional one-dimensional TIC can only provide a benign/malignant result of one pixel, and if a doctor is not satisfied with the point, a new point needs to be selected for drawing again. When relying on a TIC to determine whether a lesion is benign or malignant, the doctor can only use some local pixels as bases, but cannot have a full picture of the tumor and the breast. By using a 3D first-stage time-intensity image and a 3D second-stage time-intensity image, high latitude expansion of information is implemented. The images not only can express information of the TIC, but also can provide benign/malignant results of all pixels simultaneously, to express changes of the entire lesion region or the entire breast region, which may provide a larger amount of more complete information of benign/malignant trends of the lesion region, and changes of a plurality of lesion regions may be displayed simultaneously. In addition, a more accurate diagnosis may be performed by combining the first-stage time-intensity image and the second-stage time-intensity image in this embodiment of the present disclosure with the conventional TIC, to avoid diagnosis errors caused by only using the TIC. For example, a platform type TIC is shown in FIG. 4A, a diagnosis result tends to be benign. However, a TIC shown in FIG. 6A is of a fast-in fast-out type, and a diagnosis result tends to be malignant. It may be learned that in the same lesion region, due to selection of different pixels, different diagnosis results may be generated. However, in fact, the tumor of the lesion region is malignant. By using the first-stage time-intensity image and the second-stage time-intensity image generated in the embodiments of the present disclosure, a benign/malignant trend of the lesion region may be determined very accurately, which improves diagnosis accuracy.

Based on the foregoing embodiment, a specific application scenario is used for description in the following. The image processing method in an embodiment of the present disclosure is described by using image schematic diagrams of an implementation as an example.

Figure 7A:
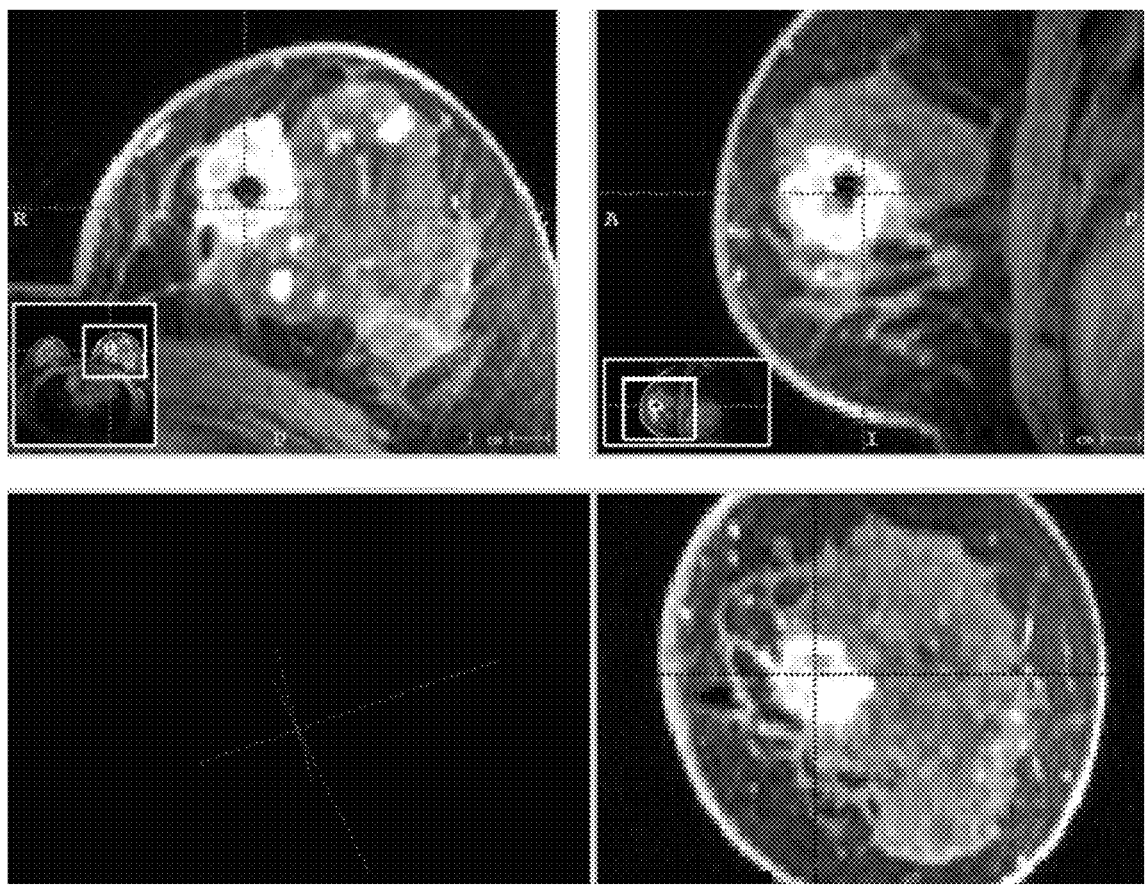
FIG. 7A is a schematic diagram of another DCE magnetic resonance image according to an embodiment of the present disclosure.

1) In the embodiments of the present disclosure, by MRI scanning, DCE magnetic resonance images of a plurality of time points for a breast may be obtained. The DCE magnetic resonance images of the plurality of time points serve as an input. FIG. 7A is a schematic diagram of another DCE magnetic resonance image according to an embodiment of the present disclosure, where an upper left image is a cross-sectional view, an upper right image is a sagittal plane view, and a lower right image is a coronal plane view, and highlighted regions on the images are lesion regions of a tumor.

Figure 7B:
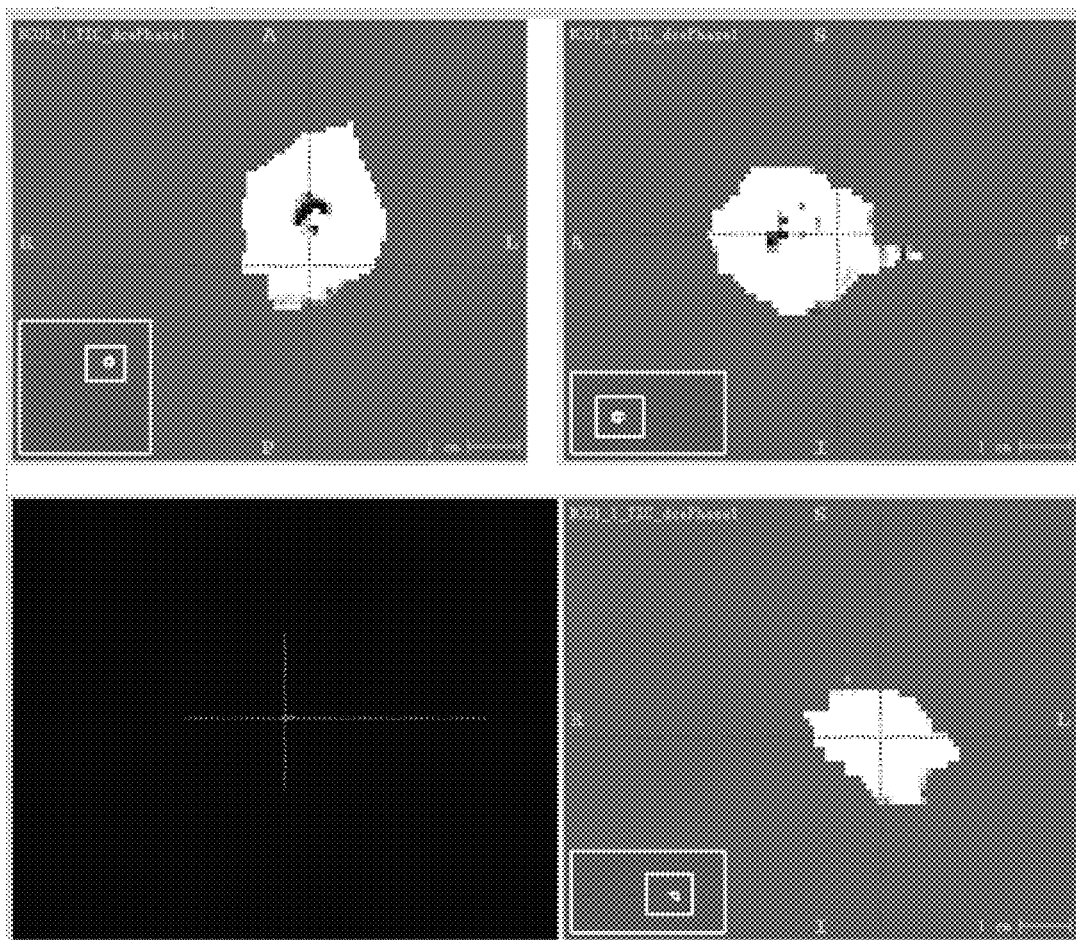
FIG. 7B is a schematic diagram of another first-stage time-intensity image before a time to peak according to an embodiment of the present disclosure.
Figure 7C:
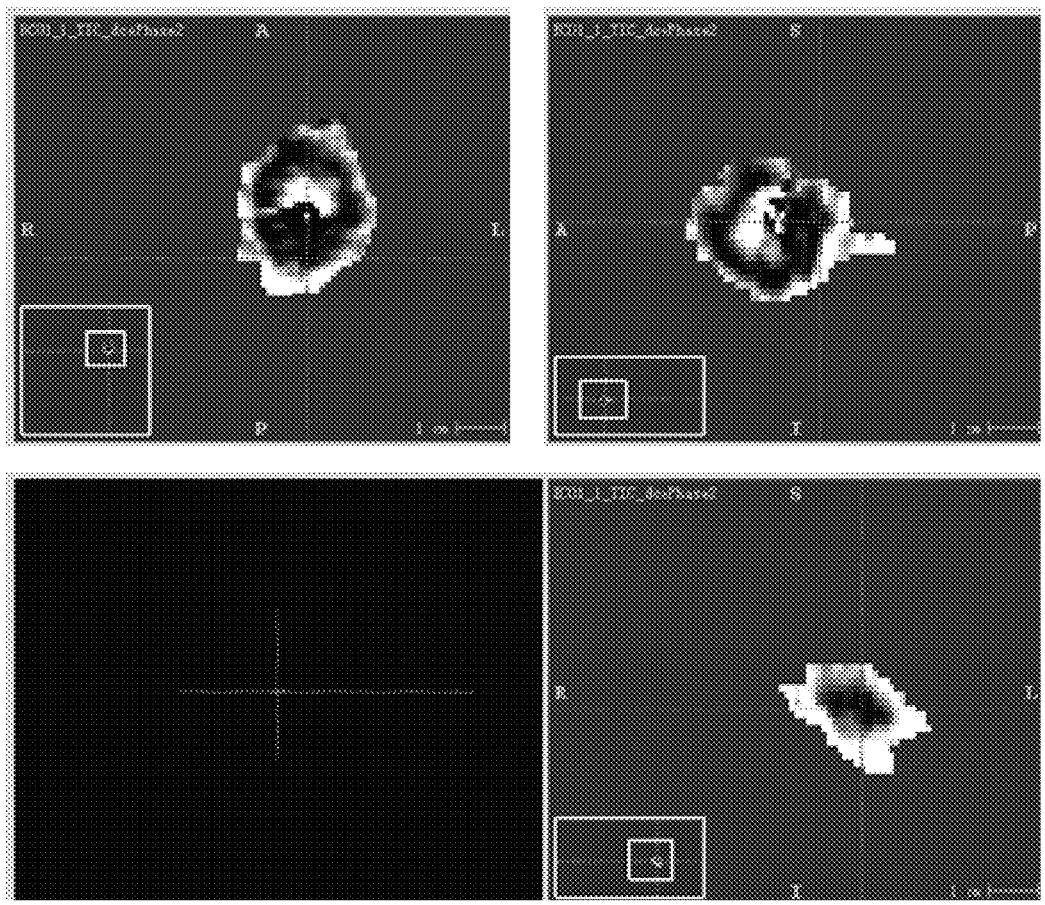
FIG. 7C is a schematic diagram of another second-stage time-intensity image after a time to peak according to an embodiment of the present disclosure.

2) Based on the inputted DCE magnetic resonance images, a time to peak is determined, and a first-stage time-intensity image before the time to peak and a second-stage time-intensity image after the time to peak are generated respectively. FIG. 7B is a schematic diagram of another first-stage time-intensity image before a time to peak according to an embodiment of the present disclosure. FIG. 7C is a schematic diagram of another second-stage time-intensity image after a time to peak according to an embodiment of the present disclosure. FIG. 7B and FIG. 7C are only schematic diagrams of a lesion region of a part of a tumor, showing changes of the lesion region of the tumor before and after the time to peak. Highlighted regions represent intensity of brightness increasing, and darker regions represent intensity of brightness decreasing. It may be seen from FIG. 7B and FIG. 7C that, the highlighted regions of the lesion region of the tumor before the time to peak represent that the blood flow-in increases intensively, and the darker regions after the time to peak represent that a blood flow-out speed is relatively high. It may be learned that the tumor is of a fast-in fast-out type, and may be determined as a malignant tumor.

Figure 8:
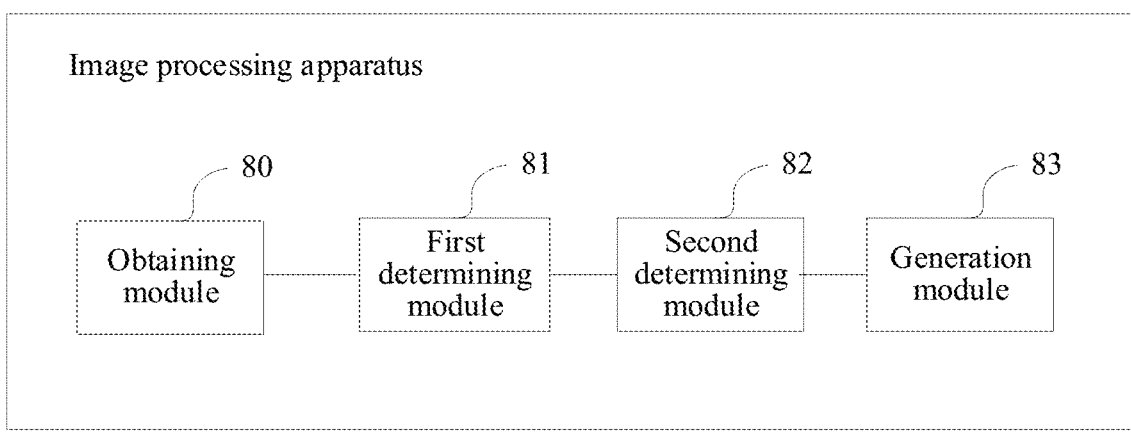
FIG. 8 is a schematic structural diagram of an image processing apparatus according to an embodiment of the present disclosure.

Based on the foregoing embodiment, an embodiment of the present disclosure further provides an image processing apparatus. As shown in FIG. 8, the image processing apparatus specifically includes:

an obtaining module 80, configured to obtain dynamic contrast enhanced (DCE) magnetic resonance images corresponding to a plurality of time points for the same detection target;

a first determining module 81, configured to determine average pixel grayscale values of images of the same lesion region in the DCE magnetic resonance images of the plurality of time points respectively;

a second determining module 82, configured to determine a time to peak according to the average pixel grayscale values corresponding to the plurality of time points; and a generation module 83, configured to generate a first-stage time-intensity image before the time to peak and a second-stage time-intensity image after the time to peak respectively according to the DCE magnetic resonance images of the plurality of time points and the time to peak, the first-stage time-intensity image and the second-stage time-intensity image being 3D images, a pixel grayscale value of each point in the first-stage time-intensity image and the second-stage time-intensity image representing a change rate of blood supply intensity and reflecting a severity level of the lesion.

In an embodiment of the present disclosure, the first determining module 81 is further configured to determine a lesion region in each of the DCE magnetic resonance images according to a preset image segmentation algorithm and lesion features.

In an embodiment of the present disclosure, when determining the time to peak according to the average pixel grayscale values corresponding to the plurality of time points, the second determining module 82 is specifically configured to:

generate a TIC of the same lesion region according to the average pixel grayscale values corresponding to the plurality of time points; and determine a first-order gradient curve corresponding to the TIC, and use a time point corresponding to a highest point on the corresponding first-order gradient curve as the time to peak.

In an embodiment of the present disclosure, when generating the first-stage time-intensity image before the time to peak and the second-stage time-intensity image after the time to peak respectively, the generation module 83 is specifically configured to:

determine a start time point and an end time point in the plurality of time points;

generate the first-stage time-intensity image before the time to peak according to a difference value between the DCE magnetic resonance image of the time to peak and the DCE magnetic resonance image of the start time point; and generate the second-stage time-intensity image after the time to peak according to a difference value between the DCE magnetic resonance image of the end time point and the DCE magnetic resonance image of the time to peak.

In an embodiment of the present disclosure, when generating the first-stage time-intensity image before the time to peak and the second-stage time-intensity image after the time to peak respectively, the generation module 83 is specifically configured to:

determine a start time point and an end time point in the plurality of time points, and sample a preset quantity of time points from the plurality of time points;

determine first difference values between the DCE magnetic resonance images of the time points sampled before the time to peak and the DCE magnetic resonance image of the start time point respectively, and generate the first-stage time-intensity image before the time to peak according to an average value of the first difference values; and determine second difference values between the DCE magnetic resonance images of the time points sampled after the time to peak and the DCE magnetic resonance image of the time to peak respectively, and generate the second-stage time-intensity image after the time to peak according to an average value of the second difference values.

The term unit (and other similar terms such as subunit, module, submodule, etc.) in this disclosure may refer to a software unit, a hardware unit, or a combination thereof. A software unit (e.g., computer program) may be developed using a computer programming language. A hardware unit may be implemented using processing circuitry and/or memory. Each unit can be implemented using one or more processors (or processors and memory). Likewise, a processor (or processors and memory) can be used to implement one or more units. Moreover, each unit can be part of an overall unit that includes the functionalities of the unit.

Figure 9:
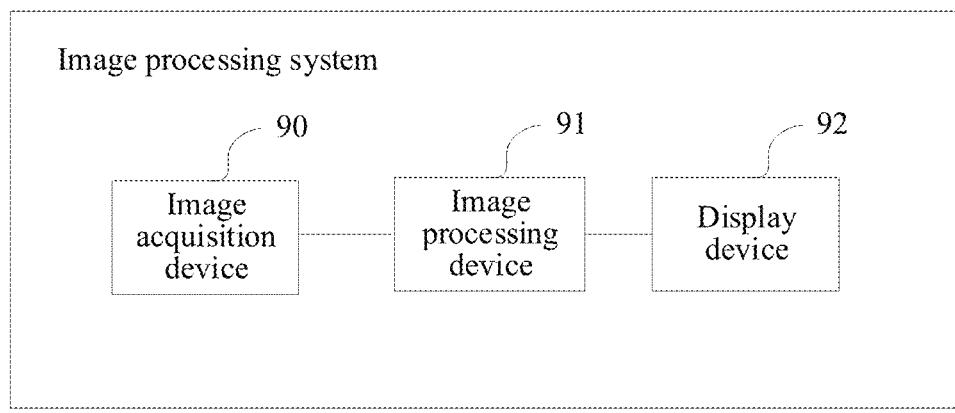
FIG. 9 is a schematic structural diagram of an image processing system according to an embodiment of the present disclosure.

Based on the foregoing embodiment, an embodiment of the present disclosure further provides an image processing system. A schematic structural diagram of the image processing system is shown in FIG. 9.

The image processing system at least includes an image acquisition device 90, an image processing device 91, and a display device 92. In an embodiment of the present disclosure, the image acquisition device 90, the image processing device 91, and the display device 92 are related medical instruments, which may be integrated into the same medical instrument, and or may be divided into a plurality of devices connected to each other for communication, to form a medical system for use. For example, for an analysis of breast MRI impact tumors, the image acquisition device 90, the image processing device 91, and the display device 92 may be integrated to be an MRI scanner.

Specifically, the image acquisition device 90 is configured to obtain DCE magnetic resonance images corresponding to a plurality of time points for the same detection target.

The image processing device 91 is configured to respectively determine average pixel grayscale values of images of the same lesion region in DCE magnetic resonance images of the plurality of time points, determine a time to peak according to the average pixel grayscale values corresponding to the plurality of time points, and generate a first-stage time-intensity image before the time to peak and a second-stage time-intensity image after the time to peak respectively according to the DCE magnetic resonance images of the plurality of time points and the time to peak, the first-stage time-intensity image and the second-stage time-intensity image being 3D images, a pixel grayscale value of each point in the first-stage time-intensity image and the second-stage time-intensity image representing a change rate of blood supply intensity and reflecting a severity level of the lesion.

Specifically, the method that the image processing device 91 processes the DCE magnetic resonance images and generates the first-stage time-intensity image and the second-stage time-intensity image is the same as the image processing method in the foregoing embodiment. Details are not described herein again.

The display device 92 is configured to output and display the first-stage time-intensity image and the second-stage time-intensity image.

Figure 10:
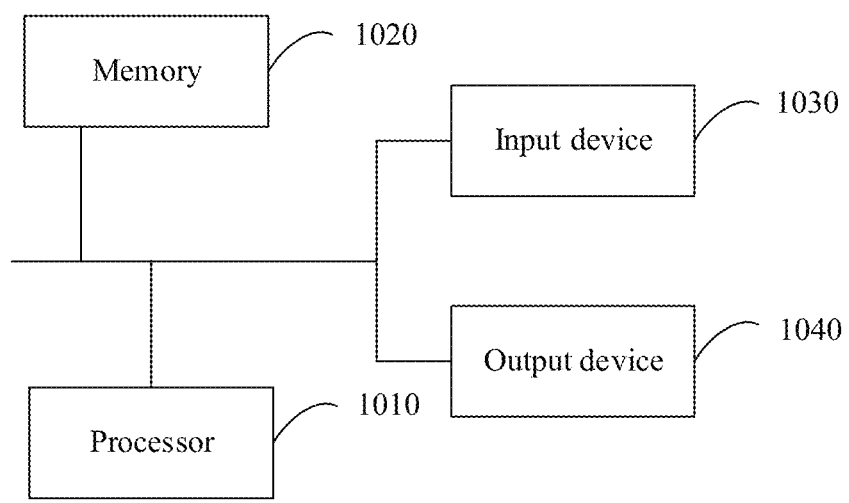
FIG. 10 is a schematic structural diagram of an electronic device according to an embodiment of the present disclosure.

Based on the foregoing embodiments, an embodiment of the present disclosure further provides an electronic device. FIG. 10 is a schematic structural diagram of the electronic device.

The electronic device provided in one embodiment of the present disclosure may include at least one center processing unit (CPU) 1010, at least one memory 1020, an input device 1030, an output device 1040, and the like. The input device 1030 may include a keyboard, a mouse, a touch screen, and the like. The output device 1040 may include a display device, such as a liquid crystal display (LCD) or a cathode ray tube (CRT).

The memory 1020 may include a read-only memory (ROM) and a random access memory (RAM), and provide program instructions and data stored in the memory 1020 for the processor 1010. In an embodiment of the present disclosure, the memory 1020 may be configured to store program instructions of an image processing method according to the embodiments of the present disclosure.

The processor 1010 invokes the program instructions stored in the memory 1020, and according to the obtained program instructions, the processor 1010 is configured to perform the following operations:

obtaining DCE magnetic resonance images corresponding to a plurality of time points for the same detection target;

determining average pixel grayscale values of images of the same lesion region in the DCE magnetic resonance images of the plurality of time points respectively;

determining a time to peak according to the average pixel grayscale values corresponding to the plurality of time points; and generating a first-stage time-intensity image before the time to peak and a second-stage time-intensity image after the time to peak respectively according to the DCE magnetic resonance images of the plurality of time points and the time to peak, the first-stage time-intensity image and the second-stage time-intensity image being 3D images, a pixel grayscale value of each point in the first-stage time-intensity image and the second-stage time-intensity image representing a change rate of blood supply intensity and reflecting a severity level of the lesion.

In an embodiment of the present disclosure, the processor 1010 is further configured to: determine a lesion region in each of the DCE magnetic resonance images according to a preset image segmentation algorithm and lesion features.

In an embodiment of the present disclosure, when determining the time to peak according to the average pixel grayscale values corresponding to the plurality of time points, the processor 1010 is specifically configured to:

generate a TIC of the same lesion region according to the average pixel grayscale values corresponding to the plurality of time points; and determine a first-order gradient curve corresponding to the TIC, and use a time point corresponding to a highest point on the corresponding first-order gradient curve as the time to peak.

In an embodiment of the present disclosure, when generating the first-stage time-intensity image before the time to peak and the second-stage time-intensity image after the time to peak respectively, the processor 1010 is specifically configured to:

determine a start time point and an end time point in the plurality of time points;

generate the first-stage time-intensity image before the time to peak according to a difference value between the DCE magnetic resonance image of the time to peak and the DCE magnetic resonance image of the start time point; and generate the second-stage time-intensity image after the time to peak according to a difference value between the DCE magnetic resonance image of the end time point and the DCE magnetic resonance image of the time to peak.

In an embodiment of the present disclosure, when generating the first-stage time-intensity image before the time to peak and the second-stage time-intensity image after the time to peak respectively, the processor 1010 is specifically configured to:

determine a start time point and an end time point in the plurality of time points, and sample a preset quantity of time points from the plurality of time points;

determine first difference values between the DCE magnetic resonance images of the time points sampled before the time to peak and the DCE magnetic resonance image of the start time point respectively, and generate the first-stage time-intensity image before the time to peak according to an average value of the first difference values; and determine second difference values between the DCE magnetic resonance images of the time points sampled after the time to peak and the DCE magnetic resonance image of the time to peak respectively, and generate the second-stage time-intensity image after the time to peak according to an average value of the second difference values.

In an embodiment of the present disclosure, the electronic device may be a medical device, mainly for medical image processing; certainly, the electronic device may alternatively be a terminal device or a server, and the image processing method is performed by the terminal device or the server.

Based on the foregoing embodiments, an embodiment of the present disclosure provides a computer-readable storage medium, storing a computer program, the computer program, when executed by a processor, implementing the image processing method according to any method embodiment described above.

A person skilled in the art can understand that the embodiments of the present disclosure may be provided as a method, a system, or a computer program product. Therefore, the present disclosure may use a form of hardware-only embodiments, software-only embodiments, or embodiments combining software and hardware. Moreover, an embodiment of the present disclosure may use a form of a computer program product that is implemented on one or more computer-usable storage media (including but not limited to a disk memory, a CD-ROM, an optical memory, and the like) that include computer-usable program code.

The present disclosure is described with reference to flowcharts and/or block diagrams of the method, the device (system), and the computer program product according to the embodiments of the present disclosure. It is to be understood that computer program instructions can implement each procedure and/or block in the flowcharts and/or block diagrams and a combination of procedures and/or blocks in the flowcharts and/or block diagrams. These computer program instructions may be provided to a general-purpose computer, a special-purpose computer, an embedded processor, or a processor of another programmable data processing device to generate a machine, so that an apparatus configured to implement functions specified in one or more procedures in the flowcharts and/or one or more blocks in the block diagrams is generated by using instructions executed by the computer or the processor of another programmable data processing device.

These computer program instructions may alternatively be stored in a computer-readable memory that can instruct a computer or another programmable data processing device to work in a specific manner, so that the instructions stored in the computer-readable memory generate an artifact that includes an instruction apparatus. The instruction apparatus implements a specific function in one or more procedures in the flowcharts and/or in one or more blocks in the block diagrams.

These computer program instructions may further be loaded onto a computer or another programmable data processing device, so that a series of operations and steps are performed on the computer or the another programmable device, thereby generating computer-implemented processing. Therefore, the instructions executed on the computer or the another programmable device provide steps for implementing a specific function in one or more processes in the flowcharts and/or in one or more blocks in the block diagrams.

Although exemplary embodiments of the present disclosure have been described, once persons skilled in the art know the basic creative concept, they can make additional changes and modifications to these embodiments. Therefore, the following claims are intended to be construed as to cover the exemplary embodiments and all changes and modifications falling within the scope of the present disclosure.

Obviously, a person skilled in the art can make various modifications and variations to the embodiments of the present disclosure without departing from the spirit and scope of the embodiments of the present disclosure. In this way, if these modifications and variations made to the embodiments of the present disclosure fall within the scope of the claims of the present disclosure and equivalent technologies thereof, the present disclosure also intends to include these changes and variations.

What is claimed is:

1. An image processing method, performed by an electronic device, the method comprising:
   obtaining dynamic contrast enhanced (DCE) magnetic resonance images corresponding to a plurality of time points for a same detection target;
   determining average pixel grayscale values of images of a same lesion region in the DCE magnetic resonance images of the plurality of time points respectively;
   determining a time to peak according to the average pixel grayscale values corresponding to the plurality of time points; and
   generating a first-stage time-intensity image before the time to peak and a second-stage time-intensity image after the time to peak respectively according to the DCE magnetic resonance images of the plurality of time points and the time to peak, the first-stage time-intensity image and the second-stage time-intensity image being 3D images, and a pixel grayscale value of each pixel in the first-stage time-intensity image and the second-stage time-intensity image representing a change rate of blood supply intensity and reflecting a severity level of a lesion corresponding to the lesion region.

2. The method according to claim 1, further comprising:
   determining the lesion region in each of the DCE magnetic resonance images according to a preset image segmentation algorithm and lesion features.

3. The method according to claim 1, wherein the determining a time to peak according to the average pixel grayscale values corresponding to the plurality of time points comprises:
   generating a time-intensity curve (TIC) of the same lesion region according to the average pixel grayscale values corresponding to the plurality of time points; and
   determining a first-order gradient curve corresponding to the TIC, and using a time point corresponding to a highest point on the first-order gradient curve as the time to peak.

4. The method according to claim 1, wherein the generating a first-stage time-intensity image before the time to peak and a second-stage time-intensity image after the time to peak respectively comprises:
   determining a start time point and an end time point in the plurality of time points;
   generating the first-stage time-intensity image before the time to peak according to a difference value between the DCE magnetic resonance image of the time to peak and the DCE magnetic resonance image of the start time point; and
   generating the second-stage time-intensity image after the time to peak according to a difference value between the DCE magnetic resonance image of the end time point and the DCE magnetic resonance image of the time to peak.

5. The method according to claim 1, wherein the generating a first-stage time-intensity image before the time to peak and a second-stage time-intensity image after the time to peak respectively comprises:
   determining a start time point and an end time point in the plurality of time points, and sampling a preset quantity of time points from the plurality of time points;
   determining first difference values between the DCE magnetic resonance images of the time points sampled before the time to peak and the DCE magnetic resonance image of the start time point respectively, and generating the first-stage time-intensity image before the time to peak according to an average value of the first difference values; and
   determining second difference values between the DCE magnetic resonance images of the time points sampled after the time to peak and the DCE magnetic resonance image of the time to peak respectively, and generating the second-stage time-intensity image after the time to peak according to an average value of the second difference values.

6. The method according to claim 1, wherein when pixel grayscale values of the lesion region in the first-stage time-intensity image are positive values and are greater than a specific threshold, and pixel grayscale values of the lesion region in the second-stage time-intensity image are negative values and are less than a specific threshold, a severity level of the lesion region is higher than a preset level.

7. The method according to claim 1, further comprising:
   setting colors corresponding to different pixel grayscale values in the first-stage time-intensity image and the second-stage time-intensity image, wherein an intensity of a first color indicates an increasing extent in brightness of a pixel grayscale value, and an intensity of a second color indicates a decreasing extent in brightness of a pixel grayscale value.

8. An electronic device, comprising:
   at least one memory, configured to store program instructions; and
   at least one processor, configured to invoke the program instructions stored in the memory, to perform a plurality of operations comprising:
   obtaining dynamic contrast enhanced (DCE) magnetic resonance images corresponding to a plurality of time points for a same detection target;
   determining average pixel grayscale values of images of a same lesion region in the DCE magnetic resonance images of the plurality of time points respectively;
   determining a time to peak according to the average pixel grayscale values corresponding to the plurality of time points; and
   generating a first-stage time-intensity image before the time to peak and a second-stage time-intensity image after the time to peak respectively according to the DCE magnetic resonance images of the plurality of time points and the time to peak, the first-stage time-intensity image and the second-stage time-intensity image being 3D images, and a pixel grayscale value of each pixel in the first-stage time-intensity image and the second-stage time-intensity image representing a change rate of blood supply intensity and reflecting a severity level of a lesion corresponding to the lesion region.

9. The device according to claim 8, wherein the plurality of operations further comprises:
   determining the lesion region in each of the DCE magnetic resonance images according to a preset image segmentation algorithm and lesion features.

10. The device according to claim 8, wherein the determining a time to peak according to the average pixel grayscale values corresponding to the plurality of time points comprises:
    generating a time-intensity curve (TIC) of the same lesion region according to the average pixel grayscale values corresponding to the plurality of time points; and
    determining a first-order gradient curve corresponding to the TIC, and using a time point corresponding to a highest point on the first-order gradient curve as the time to peak.

11. The device according to claim 8, wherein the generating a first-stage time-intensity image before the time to peak and a second-stage time-intensity image after the time to peak respectively comprises:
    determining a start time point and an end time point in the plurality of time points;
    generating the first-stage time-intensity image before the time to peak according to a difference value between the DCE magnetic resonance image of the time to peak and the DCE magnetic resonance image of the start time point; and
    generating the second-stage time-intensity image after the time to peak according to a difference value between the DCE magnetic resonance image of the end time point and the DCE magnetic resonance image of the time to peak.

12. The device according to claim 8, wherein the generating a first-stage time-intensity image before the time to peak and a second-stage time-intensity image after the time to peak respectively comprises:
    determining a start time point and an end time point in the plurality of time points, and sampling a preset quantity of time points from the plurality of time points;
    determining first difference values between the DCE magnetic resonance images of the time points sampled before the time to peak and the DCE magnetic resonance image of the start time point respectively, and generating the first-stage time-intensity image before the time to peak according to an average value of the first difference values; and
    determining second difference values between the DCE magnetic resonance images of the time points sampled after the time to peak and the DCE magnetic resonance image of the time to peak respectively, and generating the second-stage time-intensity image after the time to peak according to an average value of the second difference values.

13. The device according to claim 8, wherein when pixel grayscale values of the lesion region in the first-stage time-intensity image are positive values and are greater than a specific threshold, and pixel grayscale values of the lesion region in the second-stage time-intensity image are negative values and are less than a specific threshold, a severity level of the lesion region is higher than a preset level.

14. The device according to claim 8, wherein the plurality of operations further comprises:
    setting colors corresponding to different pixel grayscale values in the first-stage time-intensity image and the second-stage time-intensity image, wherein an intensity of a first color indicates an increasing extent in brightness of a pixel grayscale value, and an intensity of a second color indicates a decreasing extent in brightness of a pixel grayscale value.

15. A non-transitory computer-readable storage medium, storing a computer program, the computer program, when executed by a processor, cause the processor to perform a plurality of operations comprising:
    obtaining dynamic contrast enhanced (DCE) magnetic resonance images corresponding to a plurality of time points for a same detection target;
    determining average pixel grayscale values of images of a same lesion region in the DCE magnetic resonance images of the plurality of time points respectively;
    determining a time to peak according to the average pixel grayscale values corresponding to the plurality of time points; and
    generating a first-stage time-intensity image before the time to peak and a second-stage time-intensity image after the time to peak respectively according to the DCE magnetic resonance images of the plurality of time points and the time to peak, the first-stage time-intensity image and the second-stage time-intensity image being 3D images, and a pixel grayscale value of each pixel in the first-stage time-intensity image and the second-stage time-intensity image representing a change rate of blood supply intensity and reflecting a severity level of a lesion corresponding to the lesion region.

16. The storage medium according to claim 15, wherein the plurality of operations further comprises:
    determining the lesion region in each of the DCE magnetic resonance images according to a preset image segmentation algorithm and lesion features.

17. The storage medium according to claim 15, wherein the determining a time to peak according to the average pixel grayscale values corresponding to the plurality of time points comprises:
    generating a time-intensity curve (TIC) of the same lesion region according to the average pixel grayscale values corresponding to the plurality of time points; and
    determining a first-order gradient curve corresponding to the TIC, and using a time point corresponding to a highest point on the first-order gradient curve as the time to peak.

18. The storage medium according to claim 15, wherein the generating a first-stage time-intensity image before the time to peak and a second-stage time-intensity image after the time to peak respectively comprises:
    determining a start time point and an end time point in the plurality of time points;
    generating the first-stage time-intensity image before the time to peak according to a difference value between the DCE magnetic resonance image of the time to peak and the DCE magnetic resonance image of the start time point; and
    generating the second-stage time-intensity image after the time to peak according to a difference value between the DCE magnetic resonance image of the end time point and the DCE magnetic resonance image of the time to peak.

19. The storage medium according to claim 15, wherein the generating a first-stage time-intensity image before the time to peak and a second-stage time-intensity image after the time to peak respectively comprises:
- determining a start time point and an end time point in the plurality of time points, and sampling a preset quantity of time points from the plurality of time points;
- determining first difference values between the DCE magnetic resonance images of the time points sampled before the time to peak and the DCE magnetic resonance image of the start time point respectively, and generating the first-stage time-intensity image before the time to peak according to an average value of the first difference values; and
- determining second difference values between the DCE magnetic resonance images of the time points sampled after the time to peak and the DCE magnetic resonance image of the time to peak respectively, and generating the second-stage time-intensity image after the time to peak according to an average value of the second difference values.

20. The storage medium according to claim 15, wherein when pixel grayscale values of the lesion region in the first-stage time-intensity image are positive values and are greater than a specific threshold, and pixel grayscale values of the lesion region in the second-stage time-intensity image are negative values and are less than a specific threshold, a severity level of the lesion region is higher than a preset level.

* * * * *